(12) United States Patent
Lecourt

(10) Patent No.: US 6,592,848 B1
(45) Date of Patent: Jul. 15, 2003

(54) MIXTURES OF OXYGEN AND HELIUM FOR THE TREATMENT OF RESPIRATORY INSUFFICIENCY

(75) Inventor: Laurent Lecourt, Sevres (FR)

(73) Assignee: Air Liquide Sante (International), Paris Cedex (FR)

( * ) Notice: Subject to any disclaimer, the term of this patent is extended or adjusted under 35 U.S.C. 154(b) by 11 days.

(21) Appl. No.: 09/609,372

(22) Filed: Jul. 3, 2000

(30) Foreign Application Priority Data

Jul. 2, 1999 (FR) .............................. 99 08563

(51) Int. Cl.⁷ .............................. A61L 9/04; A61K 9/14
(52) U.S. Cl. ........................ 424/45; 424/46; 128/200.23
(58) Field of Search ................. 424/45, 46; 128/200.23

(56) References Cited

U.S. PATENT DOCUMENTS

| | | |
|---|---|---|
| 3,682,165 A | 8/1972 | Eklund |
| 3,815,591 A | 6/1974 | Schreiner et al. |
| 5,228,434 A | 7/1993 | Fishman |
| 5,542,935 A | 8/1996 | Unger et al. |
| 5,570,683 A | 11/1996 | Zapol |
| 6,001,332 A | 12/1999 | Garrett |
| 6,090,800 A | 7/2000 | Unger et al. |

FOREIGN PATENT DOCUMENTS

| | | |
|---|---|---|
| EP | 0 244 285 | 11/1987 |
| EP | 0 639 378 | 2/1995 |
| EP | 0 727 219 | 8/1996 |
| WO | 95/16484 | 6/1995 |
| WO | 95/20411 | 8/1995 |

OTHER PUBLICATIONS

C. Choux et al., Helium–Oxygen Mixture: Pre–hospitalization Care of Acute Asthma: Prospective study: SAMU 69 (Oct. 1991–Dec. 1992), *Urgences Medicales, FR, Pari, XP002074498*.

Gluck et al., "Helium–Oxygen Mixtures In Intubated Patients With Status Asthmaticus and Respiratory Acidosis" Sep. 1, 1990, vol. 98, No. 3, *Chest, US, Park Ridge, IL, XP002074496*, pp. 693–698.

*Primary Examiner*—Jose' G. Dees
*Assistant Examiner*—Robert DeWitty
(74) *Attorney, Agent, or Firm*—Young & Thompson

(57) ABSTRACT

The invention relates to a ready-to-use binary gaseous mixture containing 63.1 to 69.9% by volume of helium and the remainder being oxygen, preferably a mixture of 65% of helium and of 35% of oxygen, and its use in the treatment of asthma, of obstructive bronchopneumopathies and the like. Such a gaseous mixture can be used as a vector or propellant gas for medicinal aerosols, in particular aerosols containing a therapeutically effective substance chosen from $\beta_2$-mimetics, corticoids and anticholinergics.

3 Claims, No Drawings

MIXTURES OF OXYGEN AND HELIUM FOR THE TREATMENT OF RESPIRATORY INSUFFICIENCY

The invention describes a binary gaseous mixture consisting of helium and oxygen and its use for manufacturing the whole or part of a gaseous inhalable medicament intended for treating or preventing respiratory insufficiency situations, in particular acute asthma, chronic obstructive bronchopneumopathy (COBP) and any other clinical manifestation linked to bronchial obstruction in humans or animals.

It is known that in the case of asthma and of several other similar obstructive pathologies, bronchoconstiction and inflammatory rearrangements of the bronchial mucosa, on the one hand, and hypersecretion of mucus, on the other hand, bring about an increase in the resistance of the airways to the flow of gaseous respiratory streams, mainly air.

At the level of the airways of a human being or of an animal, it is generally considered that the flow is laminar if the Reynolds number is less than 2000 and turbulent if the Reynolds number is greater than 4000.

For example, at the level of the bronchospasm, the laminar flow of the gas becomes turbulent.

Because of this, aerodynamic resistances in relation to this flow are generated and add to the anatomical aerial resistances.

This then causes an additional respiratory work on the part of the patient because they are forced to increase their respiratory work in order to succeed in maintaining inspiratory and expiratory rate constants.

This excessive work will then rapidly cause overworking and an exaggerated tiredness of the respiratory muscles; the laminal aerial flow gradually disappearing.

Another consequence of this bronchospasm is a less good ventilation because of the lower passage of air and the appearance of a hypoxemia because of the virtual constance of the shunt effect, as defined by Physiopathologie Respiratoire; John B. West; Ed. Pradel; Chap. II; p. 29; 1988.

To try to solve these problems, it has already been suggested to use helium or a mixture of oxygen and helium as respiratory gas to be administered to the patient in order to facilitate gaseous flow.

Indeed, it has thus been possible to observe clinical improvements with a helium/oxygen mixture.

However, it should be noted that they are due exclusively to the physical properties of the helium/oxygen mixture because helium is a biologically inactive rare gas which does not possess any inherent anti-inflammatory or bronchodilatory activity.

The presence of helium makes it possible to lower the density of the gaseous mixture.

It follows that, under these conditions, the value of the Reynolds number is reduced simply because of the density characteristics of the gas and the flow then takes place according to a laminar mode in place of a turbulent mode.

The helium/oxygen mixture improves the patient's comfort, reduces dyspnea, increases the available time for expiration and will thereby increase the removal of $CO_2$, as explained by the document P. Jolliet; D. Tassaux; J. C. Chevrolet; J. Vincent; Ed. *Yearbook of intensive care and emergency medicine;* Berlin; Heidelberg; New York; London; Paris; Springer Verlag, 1999; 244–251.

In addition, there may be mentioned in particular the document Barach et al.; *Use of helium as a new therapeutic gas;* Proc. Soc. Exp. Bio. Med., 1934; 32: 462–464, which teaches a beneficial effect of gaseous helium and oxygen mixtures in patients suffering from obstructive pulmonary diseases.

Moreover, numerous publications deal with the use of gaseous helium in asthma and COBP, but most of these articles are series of clinical cases, in which the methodology for execution is often open to criticism.

Thus, the following documents may be mentioned:

T. S. Lu, et al.; *Helium/Oxygen in the treatment of upper airway obstruction;* Anesthesiology 1976; 45: 678–680;

S. T. Shiue et al.; *The use of helium-oxygen mixture in the support of patients with status asthmaticus and respiratory acidosis;* J. Asthma 1989; 26: 177–180;

J. E. Kass et al.; *Heliox therapy in acute severe asthma;* Chest 1995; 107: 757–760;

M. R. Wolfson et al.; *Mechanics and energetics of breathing helium in infants with bronchopulmonary dysplasia;* J. Pediatr. 1984; 104: 752–757;

R. A. Sauder et al.; *Helium-oxygen and conventional mechanical ventilation in the treatment of large airway obstruction and respiratory failure in an infant;* South. Med. J.; 1991; 84: 646–648;

C. Elleau et al.; *Helium-oxygen mixture in respiratory distress syndrome: a double blind study;* J. Pediatr, 1993; 122: 132–136;

D. M. Swidwa et al.; Saidel G M; *Helium-oxygen breathing in severe chronic obstructive pulmonary disease;* Chest 1985; 87: 790–795;

C. A. Manthous et al.; *Heliox improves pulsus paradoxus and peak expiratory flow in nonintubated patients with severe asthma;* Am. J. Respir. Crit. Care Med; 1995; 151: 310–314; and F. Martin; *Utilisation de mélanges Hélium/Oxygène au cours de létat de mal asthmatique* (Use of Helium/Oxygen mixtures during the asthma illness); Rev. Pneumol. Clin. 1987; 43: 186–189.

In addition, two publications relate to the use of oxygen/helium mixtures in acute asthma patients, namely: *Evaluation of Heliox in children hospitalized with acute severe asthma;* Chest 1996; 109: 1256–61, and Kudukis et al.; *Inhaled Helium-oxygen revisited; Effect of inhaled Helium-oxygen during the treatment of status asthmaticus in children;* J. Pediatr. 1997; 130: 217–24.

The use of a mixture with 80% of helium and 20% of oxygen shows a decrease in the paradoxical pulse rate and an increase in the peak respiratory rate in these patients.

In addition, the document EP-A-741588 describes the use of a gas containing helium and/or neon as medicinal aerosol vector for the treatment of asthma. According to this document, the proportion of helium in the gas is greater than or equal to 70%. It should be noted that similar results had already been obtained and reported by the document M. Svartengren et al.; *Human Lung Deposition of Particles Suspended in Air or in Helium/Oxygen Mixture;* Exp. Lung. Research, 15: 575–585, 1989; as well as by the document A. Malanga et al.; *Heliox Improves Rate of Response to aerosol bronchodilator;* Am. Review of Resp. Dis.; International Conference Supplement, Vol. 147, No. 4, April 1993, A65.

Moreover, it is also possible to mention the document EP-A-639378 describing the therapeutic use of a gaseous mixture consisting of 30 to 50% by volume of oxygen, and the remainder being helium supplemented with 2 to 20 vpm of nitrogen monoxide (NO).

By contrast, the document EP-A-868921 describes a gaseous mixture comprising from 20 to 70% of oxygen, from 1 to 8% of carbon dioxide ($CO_2$) and the balance being helium, which can be used for detecting or treating tumors.

The document EP-A-727219 teaches, for its part, a gaseous mixture consisting of 20 to 40% of oxygen, 2 to 10% of carbon dioxide, and the remainder being helium, which can be used for treating asthma.

The following documents may also be mentioned:

*Helium-Oxygen Mixtures in Intubated Patients with Status Asthmaticus and Respiratory Acidosis;* E. H. Gluck et al.; CHEST/98/3/September 1990, p. 693–698, which describes the physical properties of several respiratory mixtures consisting of 20% of helium and 80% of oxygen, 40% of helium and 60% of oxygen, or 80% of helium and 20% of oxygen, in particular the beneficial effect of these mixtures for reducing barotraumas and improving the ventilation of patients.

U.S. Pat. No. 5,228,434 relating to an anesthetic gas consisting of 60 to 78.5 mol % of xenon, 19.5 to 38 mol % of oxygen and 2.5 to 20.5 mol % of helium.

EP-A-0244285 relating to the use of nitrous oxide ($N_2O$) mixed with oxygen and optionally helium for producing a nonhypoxia-causing gaseous mixture which can be used as a product for the radiosensitization of biological tissues in radiotherapy.

Mélange hélium-oxygène prise en charge préhospitalière des asthmes aigus graves. Etude prospective (Helium-oxygen mixture, prehospital management of severe acute asthma. Prospective study): SAMU 69. BSPP Conference, C. Choux et al., October 1991–December 1992, which describes the use of binary gaseous mixtures consisting of 78% of helium and 22% of oxygen in the treatment of asthma.

U.S. Pat. No. 3,682,165 relating to a gas for deepsea diving consisting of 60% of helium and 40% of oxygen.

U.S. Pat. No. 3,815,591 also relating to a gas for deepsea diving consisting of 63% of helium and 37% of oxygen.

In the light of the prior art, several theoretical arguments are in favor of the administration of gaseous mixtures based on helium, namely in particular:

reduction in the respiratory work better elimination of the expired $CO_2$ at the level of the tracheobronchial tree, and enhanced laminar flow.

Furthermore, because of the consistency and the extent of the shut effect, the addition of oxygen to the gaseous mixture is obligatory.

However, as is evident from the above documents, up until now, it was customary and recommended to use, for treating patients, gaseous mixtures containing at least 70 to 75% of helium and/or from 20 to 25% of oxygen, optionally supplemented with other constituents reputed to be therapeutically active, such as nitrogen monoxide (NO) as taught by EP-A-639378, or carbon dioxide ($CO_2$) as described by EP-A-727219.

However, it has been demonstrated that the use of conventional mixtures based on helium and oxygen comprising between 20 to 25% of oxygen is not sufficient to provide sufficient oxygenation of the patient in the majority of situations.

It is therefore necessary to have a second bottle of oxygen and to administer this oxygen by a second route, concomitantly with the administration of the $O_2$/He mixture.

However, it can be immediately understood that the requirement to add oxygen from another bottle poses several problems and has numerous drawbacks, in particular:

difficulty of correctly monitoring the $FiO_2$, that is to say the fraction of inspired oxygen which is really administered to the patient, risk of losing the benefits of the action of helium: the lower the percentage of helium, the lower its physical effect, risk of toxicity of oxygen in high concentration, handling, storage and use of oxygen under medical supervision, obligation to have two bottles, causing problems during the use of this mixture by mobile emergency units of the SAMU type, setting and calibration of the ventilators for more difficult mechanical and noninvasive ventilation, safety of the patient, and increased surveillance by the medical staff during administration to the patient.

Hence, the aim of the present invention is to solve and/or palliate all or some of the abovementioned disadvantages by providing in particular an improved gaseous mixture and its use for the manufacture of a gaseous medicament intended for treating or preventing respiratory pathologies, in particular acute asthma and COBPs.

The invention therefore relates to a ready-to-use binary aqueous mixture consisting of 63.1 to 69.9% by volume of helium and the remainder being oxygen, said gaseous mixture being packaged at a pressure greater than 2 bar.

In general, in the context of the present invention, the gaseous $He/O_2$ mixture is binary, that is to say that the sum of the respective proportions of helium and oxygen in the gaseous mixture is approximately equal and, preferably, equal to 100% (the % being % by volume), with the exception of the possible presence of unavoidable gaseous impurities which can result from the process for the manufacture of the gaseous mixture or of its constituents, for example impurities of the CO, $CO_2$, $H_2O$ and $N_2$ type, and the like.

Depending on the case, the gaseous mixture may comprise one or more of the following characteristics:

it consists of 63.2 to 69.8% of helium and the balance being oxygen, preferably from 63.3 to 69.5% of helium, the remainder being oxygen.

it consists of 63.5 to 69% of helium and the balance being oxygen, preferably it consists of 64 to 68% of helium, the remainder being oxygen.

it consists of 64 to 67% of helium, the remainder being oxygen, preferably from 64 to 66% of helium, the remainder being oxygen.

is packaged at a pressure of between 2 and 300 bar, preferably between 50 and 300 bar, preferentially between 100 and 250 bar.

The invention also relates to the use of a gaseous mixture consisting of 61 to 69.9% by volume of helium, preferably between 61 and 69% by volume of helium, and the remainder being oxygen for the manufacture of at least a portion of an inhalable gaseous medicament for treating or preventing a pathology of the upper airways in humans or animals.

Moreover, the invention also relates to the use of a gaseous mixture consisting of 61 to 69.9% by volume of helium, preferably between 61 and 69% by volume of helium, and the remainder being oxygen for the manufacture of at least a portion of an inhalable gaseous medicament for treating or preventing asthma, in particular acute asthma, in humans or animals.

Likewise, the invention relates, in addition, to the use of a gaseous mixture consisting of 61 to 69.9% by volume of helium, preferably between 61 and 69% by volume of helium, and the remainder being oxygen for the manufacture of at least a portion of an inhalable gaseous medicament for treating or preventing an obstructive bronchopneumopathy in humans or animals.

Furthermore, the invention relates to the use of a gaseous mixture consisting of 61 to 69.9% by volume of helium, preferably between 61 and 69% by volume of helium, and the remainder being oxygen for the manufacture of at least a portion of a gaseous medicament for facilitating or reducing the respiratory work of a person in the weaning phase, subsequent to a period of mechanical ventilation.

In addition, the invention also relates to the use of a gaseous mixture consisting of 61 to 69.9% by volume of helium, preferably between 61 and 69% by volume of helium, and the rest being oxygen for the manufacture of at least a portion of an aerosol comprising, in addition, at least one therapeutically effective medicinal compound, preferably in liquid form and/or in solid form, for example a powder.

According to another aspect, the invention also relates to a process for converting a medicament or a medicinal compound to a form which can be used for the administration of the medicament by the respiratory tracts of mammals, in which a liquid and/or a powder containing or consisting of at least one medicament is converted to an aerosol which contains small particles of liquid and/or of powder with the aid of a gaseous stream or alternatively with the aid of other means, and in which the particles of liquid and/or of powder are collected in the gaseous stream or alternatively in a gas stream, respectively, wherein the particles of liquid are collected in a gaseous mixture consisting of 61 to 69.9% by volume of helium, preferably between 61 and 69% by volume of helium, and the remainder being oxygen.

According to yet another aspect, the invention relates to the medicinal preparation in the form of an aerosol comprising a vector and/or propellant gas and liquid and/or solid particles containing at least one therapeutically effective compound, wherein the vector and/or propellant gas is a gaseous mixture consisting of 61 to 69.9% by volume of helium, preferably between 61 to 69% by volume of helium, and the remainder being oxygen.

Preferably, the therapeutically effective compound is chosen from the following therapeutic or drug categories: $\beta_2$-mimetics, corticoids and anticholinergics, for example the following commercially available medicaments: BRICANYL™, ADRENALIN™, ADRENALIN™, VENTOLIN™, BECOTIDE™ and LOMUDAL™.

According to the use or the preparation envisaged, the gaseous mixture consists of 62 to 68% of helium and the balance being oxygen, preferably from 63.1 to 68% of helium and the balance being oxygen, still more preferably of 65% of helium and of 35% of oxygen approximately, preferentially from 63.5 to 68% of helium and the balance being oxygen, still more preferably from 64 to 67.5% of helium and the balance being oxygen, preferably of 65% of helium and of 35% of oxygen approximately.

The invention also covers a gas container, in particular a gas bottle, under pressure, comprising a gaseous mixture according to the invention, as well as an installation for administering a gaseous mixture according to the invention to a patient, comprising at least one gas container, and at least one ventilator for respiratory assistance in fluidic communication with at least said gas container by means of at least one gas pipe.

Likewise, the invention also relates to an installation for administering a gaseous mixture according to the invention to a patient, comprising at least one gas container and at least one nasal and/or buccal interface, preferably a respiratory mask, in fluidic communication with at least said gas container by means of at least one gas pipe.

In general, the 65% He+35% $O_2$ gaseous mixture of the invention is preferred.

Clinical trials have been made it possible to show the efficiency of the gaseous mixtures according to the invention during their use in clinical situations linked to excessive fatigue of the respiratory muscles because the benefit of the gaseous mixture of the invention is that it allows less fatigue of the respiratory muscles of the patient or sick person, in particular during the use of the gaseous mixture of the invention in a post-extubation phase in patients weakened by a long mechanical ventilation or a ventilation in patients with chronic respiratory insufficiency and the like.

What is claimed is:

1. A package containing ready-to-use gaseous mixture at a pressure greater than 2 bar, said mixture consisting of 63.1 to 69.9% by volume of helium, balance oxygen.

2. A package as claimed in claim 1, wherein said helium is 63.1 to 68% by volume, balance oxygen.

3. A package as claimed in claim 2, wherein said helium is 63.5 to 68% by volume, balance oxygen.

* * * * *